United States Patent [19]

Moore

[11] Plant 5,111

[45] Sep. 27, 1983

[54] ROSE PLANT

[75] Inventor: Ralph S. Moore, Visalia, Calif.

[73] Assignee: Sequoia Nursery, Visalia, Calif.

[21] Appl. No.: 344,032

[22] Filed: Jan. 29, 1982

[51] Int. Cl.[3] ..... A01H 5/00

[52] U.S. Cl. ..... Plt./8

[58] Field of Search ..... Plt./8

*Primary Examiner*—Robert E. Bagwill

[57] ABSTRACT

This invention relates to a new and distinct variety of miniature rose plant primarily identified by its white flowers born in clusters on vigorous upright plant.

1 Drawing Figure

1

The present invention relates to a new and distinct variety of hardy, dwarf, bush type rose plant of the miniature class; the variety being primarily characterized — as to novelty — by the white buds and flowers which are born in clusters on rather stiff stems.

The variety is further characterized by:

An abundance of bloom, with flowers usually borne several to the stem in small clusters.

Little or no fragrance.

A plant which is vigorous, of rounded, upright shape with small semi-glossy to glossy foliage with pointed leaflets; the buds being similar in form to Jet Trail (miniature — U.S. Plant Pat. No. 2,683) and flowers being similar in form to Green Ice (miniature — not patented).

The plant, which has a normal height of 12–14 inches (or more) can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between an un-named seedling (Rosa Wichuriana X Floradora) as the seed parent and Jet Trail (Miniature — U.S. Plant Pat. No. 2,683) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature.

*Variety identification.*—MORwhit (Commercial synonym: Little Eskimo).

Flowers borne: Several together in spray or cluster on stiff wirey stems.

Quantity of bloom: Abundant both outside and in greenhouse.

2

Bud:

*Peduncle.*—Medium to short length; slender but sturdy; erect; medium green, sometimes tinted bronze (outdoors); with few or no prickles and some short fuzz-like hairs.

*Before calyx breaks.*—Size — small. Form long, pointed, with several small foliaceous apendages on surface of bud; with foliaceous parts extending beyond the tip of bud equal to about one-half or less of its length. Color — medium green, occasionally tinted with bronze (outdoors).

*As calyx breaks.*—Color — white or greenish yellow. Opening: opens well in all weather.

Bloom:

*Size when fully open.*—Small, averaging about 30–35 mm (1¼").

*Petalage.*—Double — averaging about 40 (or more) petals, arranged regularly plus several small petaloids.

*Form.*—Cupped at first becoming flat with petals rolled slightly outward and downward. Open flowers usually have few or no stamens.

*Petals.*—Fairly thick; satiny on inside and on outside surface.

*Shape.*—Outside petals, broad lanceolate with acute tip; intermediate — lanceolate with acute tip; inside — lanceolate with acute tip.

*Color.*—Newly opened flower from a plant grown in plastic greenhouse (November 1980), Visalia, Calif.:

*Outside petal.*—Outside surface — white or near white with small yellowish area at base. Inside surface — similar color to outside surface.

*Intermediate petal.*—Outside surface similar to outside petal. Inside surface similar to outside petal.

*Inner petal.*—Outside surface — similar to intermediate petal; inside surface — similar to intermediate petal. General color effect; buds and newly opened flowers — white — inner petals may be creamy color to white. Three days open — color — similar to fresh open flowers, but entirely white. Behavior — opens well in all weather. Spent petals or flowers drop off. Flower longevity (July–August 1980) — Plant in pot 6–10 days or longer. Cut flowers at living room temperature 5–7 days or longer. Note: Mature flowers may become slightly greenish as they age.

Reproductive organs:

*Stamens.*—Few — usually none.

*Filaments.*—Varying length (if present).

*Anthers.*—Yellow (if present).

*Pollen.*—Little or none.
*Pistils.*—Average number.
*Styles.*—Varying length, near white, bunched.
*Ovaries.*—All enclosed in calyx.
*Hips.*—Few or none.
*Sepals.*—Permanent; spear shaped; recurved.
*Seed.*—One per hip (if present).

Foliage:

*Leaves.*—Compound of five (sometimes three or seven) leaflets; medium small; leathery; semi-glossy to glossy.

*Leaflets.*—Shape: broad, lanceolate, apex acute; base — rounded — sometimes acute. Color: medium green; new growth — normal (medium) green. Rachis: medium strength; upperside usually smooth; grooved; underside may have several small thorns (or claws) and few or no hairs. Stipules: short length; medium width; short length narrow points which turn out usually at about 45 degrees or more.

Growth:

*Habit.*—Dwarf; bushy; upright; much branched.
*Growth.*—Vigorous; internodes short.
*Canes.*—Medium; slender; sturdy.
*Main stems.*—Color: medium green.

*Thorns.*—Several — slender, rather long, brown. Hairs — few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers which are essentially white, the bud being pointed in the early opening stage, resembling in form Jet Trail (miniature — U.S. Plant Pat. No. 2,683), with the full open flower being rather flat with many (40 or more) petals ranging from long (outer petals) to quite short (inner petals); and further characterized by a plant of compact, vigorous, upright shape, with main stems and shoots of average thorniness, the said plant being easy to propagate from softwood cuttings; with an abundance of small semi-glossy to glossy foliage, the flowers being born usually several to the stem in clusters.

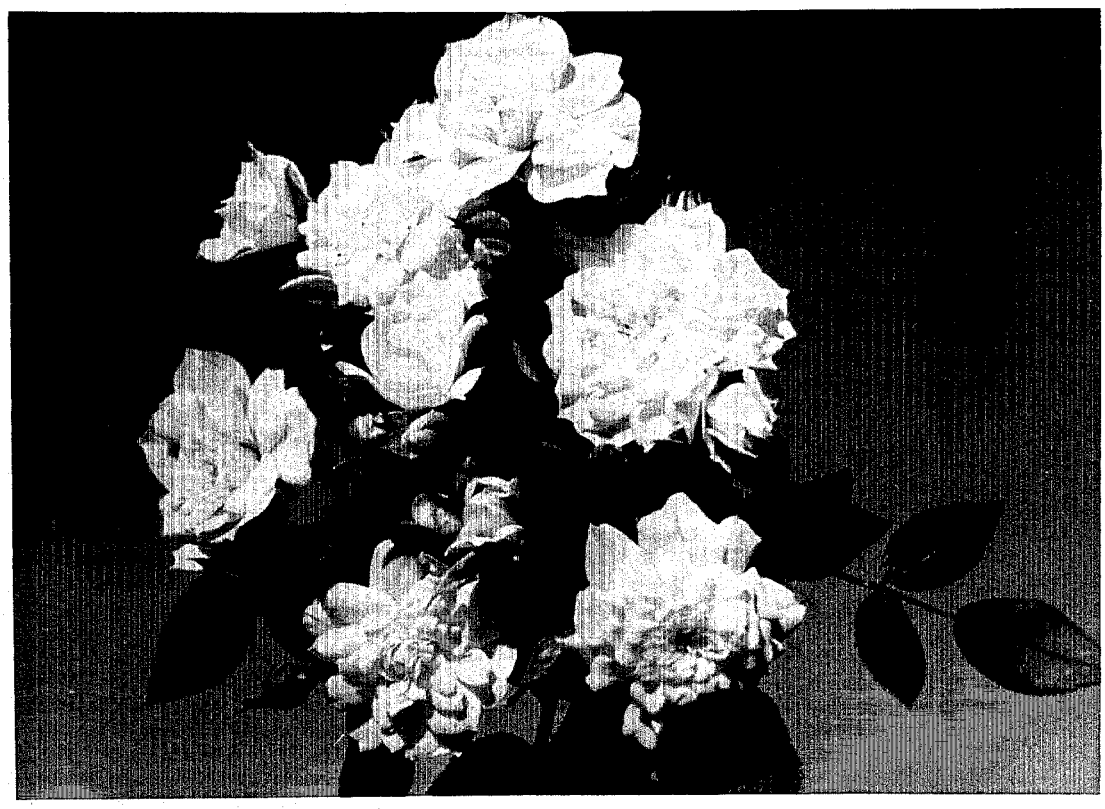

* * * * *